(12) United States Patent
Inoue et al.

(10) Patent No.: US 12,383,476 B2
(45) Date of Patent: Aug. 12, 2025

(54) W/O/W EMULSION COMPOSITION

(71) Applicant: Shiseido Company, Ltd., Tokyo (JP)

(72) Inventors: Haruhiko Inoue, Tokyo (JP); Masaki Kitajima, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 584 days.

(21) Appl. No.: 17/766,060

(22) PCT Filed: Oct. 1, 2020

(86) PCT No.: PCT/JP2020/037426
§ 371 (c)(1),
(2) Date: Apr. 1, 2022

(87) PCT Pub. No.: WO2021/066098
PCT Pub. Date: Apr. 8, 2021

(65) Prior Publication Data
US 2022/0362112 A1   Nov. 17, 2022

(30) Foreign Application Priority Data

Oct. 4, 2019   (JP) ................................. 2019-184117

(51) Int. Cl.
| | | |
|---|---|---|
| *A61K 8/06* | (2006.01) | |
| *A61K 8/25* | (2006.01) | |
| *A61K 8/34* | (2006.01) | |
| *A61K 8/81* | (2006.01) | |
| *A61K 8/92* | (2006.01) | |

(52) U.S. Cl.
CPC ............ *A61K 8/066* (2013.01); *A61K 8/25* (2013.01); *A61K 8/345* (2013.01); *A61K 8/8129* (2013.01); *A61K 8/92* (2013.01)

(58) Field of Classification Search
CPC .......... A61K 8/066; A61K 8/25; A61K 8/345; A61K 8/8129; A61K 8/92
See application file for complete search history.

(56) References Cited

U.S. PATENT DOCUMENTS

2004/0137019 A1*  7/2004  Nakamura ............. A61K 8/066
                                                        424/401
2004/0234477 A1   11/2004  Sakuta

FOREIGN PATENT DOCUMENTS

| JP | 11-033391 A | 2/1999 |
|---|---|---|
| JP | 2002-187834 A | 7/2002 |
| JP | 2002-275029 A | 9/2002 |
| JP | 2006-307031 A | 11/2006 |
| JP | 2014-196282 A | 10/2014 |
| WO | WO-03/024413 A1 | 3/2003 |

* cited by examiner

*Primary Examiner* — Michael P Cohen
(74) *Attorney, Agent, or Firm* — Foley & Lardner LLP

(57) ABSTRACT

A W/O/W emulsion composition comprising a large amount of silicone oil and having a high viscosity and a high stability is provided.

The W/O/W emulsion composition comprises:
  an inner aqueous phase;
  an oil phase in which the inner aqueous phase is dispersed; and
  an outer aqueous phase in which the oil phase is dispersed,
wherein
  the inner aqueous phase comprises an osmotic pressure regulator that prepares the inner aqueous phase to have a higher osmotic pressure than the outer aqueous phase,
  the oil phase comprises a silicone oil that is 0.5 times by mass or greater of the total oil phase, and a silicone-based surfactant having a silicone skeleton as a main skeleton and a hydrophilic group in a side chain, and
  the outer aqueous phase comprises a polyol and an alkyl-modified carboxyvinyl polymer.

6 Claims, No Drawings

W/O/W EMULSION COMPOSITION

RELATED APPLICATIONS

This application is the U.S. National Stage of PCT/JP2020/037426, filed Oct. 1, 2020, which claims the priority of Japanese Patent Application No. 2019-184117 filed on Oct. 4, 2019, which is incorporated herein by reference.

TECHNICAL FIELD

The present invention relates to a W/O/W emulsion composition, and particularly to a W/O/W emulsion composition thickened by making the inner aqueous phase to swell by the osmotic pressure difference between an outer aqueous phase and an inner aqueous phase.

BACKGROUND ART

In creams in the field of cosmetics, for example, systems are thickened by techniques of: adding a thickener such as a polymer, forming an α-gel by a surfactant, or increasing the ratio of the inner phase.

However, when a polymeric thickener is added, stickiness may occur easily, and thus texture may deteriorate. Moreover, a relatively large amount of a surfactant is needed for forming an α-gel in the aqueous phase. Furthermore, when the ratio of the inner phase (oil phase) is increased in an O/W emulsion composition, the oil amount increases, and thus freshness may deteriorate. Therefore, the techniques had disadvantages respectively.

Whereas, in the W/O/W emulsion compositions disclosed in Patent Literatures 1 to 3, the amount of the inner aqueous phase is made to be small at the time of production, and, after the W/O/W emulsion composition is prepared, aqueous components are transferred from the outer aqueous phase to the inner aqueous phase by the osmotic pressure difference. Therefore, a high inner phase (oil phase+inner aqueous phase) ratio can be achieved with a relatively small amount of the oil phase. Freshness can be achieved while having a high viscosity, and a unique feel of phase inversion associated with release of the inner aqueous phase can be achieved upon application.

In contrast, in W/O/W emulsion compositions, agents are added to the inner aqueous phase, so that the agents become coated with the oil phase and the outer aqueous phase; therefore, stability such as oxidation resistance can be improved.

CITATION LIST

[Patent Literature 1] Japanese Unexamined Patent Publication No. 2002-275029 A
[Patent Literature 2] Japanese Unexamined Patent Publication No. H11-33391 A
[Patent Literature 3] Japanese Unexamined Patent Publication No. 2006-307031 A

SUMMARY OF INVENTION

Technical Problem

However, W/O/W emulsion compositions of osmotic pressure regulation types had a high selectivity of oil phase components and a low flexibility of formulation; therefore, it was problematic. In particular, when a silicone oil was blended in a large amount, stability of the composition tended to deteriorate.

Solution to Problem

The present invention has been made in view of the above-mentioned problems, and an object thereof is to provide a W/O/W emulsion composition which comprises a large amount of silicone oil and has a high viscosity and a high stability.

DESCRIPTION OF EMBODIMENTS

The W/O/W emulsion cosmetic has a structure of which a W/O emulsion is dispersed in an outer aqueous phase.

[Osmotic Pressure Regulator]

In the present invention, a W/O emulsion that configure the inner phase comprises an osmotic pressure regulator in the aqueous phase which is the innermost phase. Osmotic pressure regulators are not limited in particular, and polyols having a relatively small molecular weight, or electrolytes such as polyols, amino acids, L-ascorbic acids or derivatives thereof are used preferably.

As for polyols, sugar alcohols such as maltitol and sorbitol, and polyethylene glycols are preferred.

The amino acid or derivatives thereof is preferably selected from amino acids or salts thereof that are known as general food additives or drugs listed in pharmacopeia. Examples thereof include L-alanine, β-alanine, L-arginine hydrochloride, L-aspartic acid monohydrate, L-aspartic acid, L-citrulline, L-glutamic acid, L-glutamic acid hydrochloride, L-glutamine, glycine, trimethylglycine, L-histidine, L-histidine hydrochloride monohydrate, L-hydroxyproline, L-isoleucine, L-leucine, L-lysine, L-lysine hydrochloride, L-ornithine hydrochloride, L-proline, L-phenylalanine, L-serine, L-threonine, L-tryptophan, L-tyrosine, L-valine, L-dopa, and L-α-aminobutyric acid. Among the above, glycine, L-serine, L-alanine, L-proline, and trimethylglycine are preferably used. Moreover, examples of derivatives include salts and esters.

Moreover, monovalent metal salts, i.e., salts of sodium, potassium, and lithium, and divalent metal salts such as calcium and magnesium salts can also be used as metal salts of the above-described amino acids. Among the above, sodium L-aspartate monohydrate, potassium L-aspartate dihydrate, sodium L-glutamate monohydrate, and potassium L-glutamate monohydrate are preferred.

L-ascorbic acid is generally called as vitamin C, and examples of its derivatives include: L-ascorbic acid monoalkyl esters such as L-ascorbic acid monostearate, L-ascorbic acid monopalmitate, and L-ascorbic acid monooleate; L-ascorbic acid monoesters such as L-ascorbic acid monophosphate ester and L-ascorbic acid 2-sulfate ester; L-ascorbic acid dialkyl esters such as L-ascorbic acid distearate, L-ascorbic acid dipalmitate, and L-ascorbic acid dioleate; L-ascorbic acid trialkyl esters such as L-ascorbic acid tristearate, L-ascorbic acid tripalmitate, and L-ascorbic acid trioleate; L-ascorbic acid triesters such as L-ascorbic acid triphosphate ester; and L-ascorbic acid glucosides such as L-ascorbic acid 2-glucoside. Among the above, L-ascorbic acid, L-ascorbic acid phosphate ester, L-ascorbic acid 2-sulfate ester, and L-ascorbic acid 2-glucoside are used preferably.

As for electrolytes, one type or two or more types selected from the above-described amino acids, L-ascorbic acids, and derivatives thereof is used preferably.

The blending amount of these osmotic pressure regulators is preferably 0.01 to 5% by weight, and particularly 0.1 to 3% by weight in the total amount of the composition according to the present invention. If the blending amount is too small, feel upon use does not improve. If the blending amount is too large, stability over time may deteriorate.

[Oil Component]

In the present invention, the oil component contained in the oil phase comprises a silicone oil as the main component. Other oils such as liquid oils, solid fats, waxes, hydrocarbon oils, higher fatty acids, higher alcohols, and synthetic ester oils can be used, but not limited thereto.

Examples of the silicone oils include chain polysiloxanes such as dimethylpolysiloxane, methylphenylpolysiloxane, and methylhydrogen polysiloxane, and cyclic polysiloxanes such as decamethylpolysiloxane, dodecamethylpolysiloxane and tetramethyl tetrahydrogen polysiloxane.

The silicone oil is 0.5 times by mass or greater, and preferably 0.7 times by mass or greater of the total oil phase. Examples of other liquid oils that can be blended include: avocado oil, Camellia oil, turtle oil, macadamia nut oil, corn oil, mink oil, olive oil, rapeseed oil, egg yolk oil, sesame oil, par chic oil, wheat germ oil, Camellia sasanqua oil, castor oil, linseed oil, safflower oil, cottonseed oil, perilla oil, soybean oil, peanut oil, Camellia sinensis seed oil, kaya oil, rice bran oil, Chinese tung oil, Japanese tung oil, jojoba oil, germ oil, triglycerol, glycerol trioctanoate, and glycerol triisopalmitate.

Examples of the solid fats include: cacao butter, coconut oil, horse fat, hydrogenated coconut oil, palm oil, beef tallow, sheep tallow, hydrogenated beef tallow, palm kernel oil, lard, beef bones fat, Japan wax kernel oil, hardened oil, hoof oil, Japan wax, and hydrogenated castor oil.

Examples of the waxes include: beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl ester, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the hydrocarbon oils include: liquid paraffin, ozocerite, squalane, pristane, paraffin, ceresin, squalene, vaseline, and microcrystalline wax.

Examples of the higher fatty acids include: lauric acid, myristic acid, palmitic acid, stearic acid, behenic acid, 12-hydroxystearic acid, undecylenic acid, and tallic acid.

Examples of the higher alcohols include: cetyl alcohol, stearyl alcohol, behenyl alcohol, myristyl alcohol, and cetostearyl alcohol.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, di-penta erythritol fatty acid ester, N-alkyl glycol monoisostearate, neopentyl glycol dicaprate, diisostearyl malate, glyceryl di-2-heptyl undecanoate, trimethylol propane tri-2-ethyl hexanoate, trimethylol propane triisostearate, pentaerythritol tetra-2-ethyl hexanoate, glyceryl tri-2-ethyl hexanoate, trimethylol propane triisostearate, cetyl 2-ethylhexanoate, 2-ethylhexyl palmitate, glyceryl trimyristate, glyceride tri-2-heptyl undecanoate, castor oil fatty acid methyl ester, oleyl oleate, cetostearyl alcohol, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate.

[Silicone-Based Surfactant]

In the present invention, the inner aqueous phase and the oil phase are emulsified with a silicone-based surfactant to form a W/O emulsion.

As the silicone-based surfactant used preferably in the present invention, a silicone-based surfactant having a silicone skeleton as a main skeleton, and a hydrophilic group in a side chain is preferred.

Examples of the silicone-based surfactant that may be preferably used in particular in the present invention include PEG-9 polydimethylsiloxyethyl dimethicone.

Other than the silicone-based surfactant, surfactants having an HLB of 7 or less can be used auxiliary in the present invention.

Examples of the surfactants having an HLB of 7 or less include: sorbitan fatty acid esters such as sorbitan monolaurate, sorbitan monooleate, sorbitan monoisostearate, and sorbitan tristearate; glycerin fatty acid esters such as glycerol monostearate, and glycerol monooleate; polyoxyethylene hydrogenated castor oils such as POE (5) hydrogenated castor oil, POE (7.5) hydrogenated castor oil, and POE (10) hydrogenated castor oil; polyether-modified silicone-based surfactants such as dimethicone copolyol, cetyl dimethicone copolyol, and dimethicone copolyol crosspolymer; polyoxyalkylated glycol fatty acid ester-based surfactants; polyglyceryl fatty acid ester-based surfactants; polyhydroxystearic acid esters of polyhydric alcohols, polyhydroxystearyl polyglycerol, and cross-linked polyorganosiloxane elastomers comprising a polyoxyethylenated chain and/or a polyoxypropylenated chain.

Among the above, polyhydroxystearyl alkylated glycol which is a polyhydroxystearic acid ester of polyhydric alcohol (e.g., polyethylene glycol dipolyhydroxystearate "Arlacel P135", manufactured by ICI), polyhydroxystearyl polyglycerin ("DEHYMULUS PGPH", manufactured by Henkel AG & Co.), dimeticone copolyol which is a polyether-modified silicone-based surfactant ("Silicone SC 9450", manufactured by Shin-Etsu Chemical Co., Ltd.), a cross-linked organopolysiloxane elastomer comprising a polyoxyethylenated chain and/or a polyoxypropylenated chain ("KSG 21", manufactured by Shin-Etsu Chemical Co., Ltd.), etc. may be preferably used.

The blending amount of the surfactant is preferably 0.01 to 10% by weight, and particularly 0.1 to 7% by weight in the total amount of the emulsion composition. If the blending amount is too small, feel upon use does not improve. If the blending amount is too large, formation of a W/O/W emulsion may be unstable.

[Alkyl-Modified Carboxyvinyl Polymer]

The W/O/W emulsion composition of the present invention comprises an alkyl-modified carboxyvinyl polymer in the outer aqueous phase for dispersing the oil phase (W/O emulsion) in the outer aqueous phase.

The alkyl-modified carboxyvinyl polymer used in the present invention is an acrylic acid/alkyl methacrylate copolymer, and acts as an emulsifier and a thickener. An acrylic acid/alkyl methacrylate copolymer having a molecular weight of about 500,000 to 3,000,000 is preferred. For example, commercially available alkyl-modified carboxyvinyl polymers such as "CARBOPOL 1342", "PEMULEN TR-1" and "PEMULEN TR-2" (all manufactured by B. F. Goodrich) may be used preferably.

The blending amount of the alkyl-modified carboxyvinyl polymer is preferably 0.01 to 2% by weight in the total amount of the cosmetic of the present invention. If the blending amount is too small, stability may deteriorate. If the blending amount is too large, squeakiness or unevenness upon use may occur.

[Polyol Added to the Outer Aqueous Phase]

In the present invention, a polyol is also added to the outer aqueous phase to improve freezing-resistance in particular.

Here, since polyols also affect osmotic pressure, the polyol in the outer aqueous phase needs to be selected carefully. Glycerin, 1,3-butylene glycol, and dipropylene glycol are adopted preferably.

The blending amount of these polyols added to the outer aqueous phase is preferably 5 to 25% by mass in the composition. If it is less than 5% by mass, freezing-resistance may decrease. If it exceeds 25% by mass, the osmotic pressure difference between the inner aqueous phase and the outer aqueous phase decreases, and thus thickness decreases.

[Other Components]

Other than the above-described essential components, the W/O/W emulsion composition of the present invention may be blended with optional additional components that are usually blended in cosmetics, as necessary, in amounts that do not inhibit the effects of the present invention. Examples of such additional components include: thickeners such as cellulose, hydroxyethyl cellulose, hydroxypropyl cellulose, methyl hydroxypropyl cellulose, methyl cellulose, carboxymethyl cellulose, quince seed, carrageenan, pectin, mannan, curdlan, chondroitin sulfate, starch, galactan, dermatan sulfate, glycogen, gum Arabic, heparan sulfate, hyaluronic acid, sodium hyaluronate, gum tragacanth, keratan sulfate, chondoroitin, xanthan gum, mucoitin sulfate, hydroxyethyl guar gum, carboxymethyl guar gum, guar gum, dextran, kerato sulfate, locust bean gum, succinoglycan, caronic acid, chitin, chitosan, carboxymethyl chitin, and agar; lower alcohols such as ethanol; antioxidants such as butyl hydroxy toluene, tocopherol, and phytin; antibacterial agents such as benzoic acid, salicylic acid, sorbic acid, paraoxybenzoic acid alkyl ester, and hexachlorophene; benzoic acid-based UV absorbers such as para-aminobenzoic acid (abbreviated as PABA hereinbelow), PABA monoglycerin ester, N,N-dipropoxy PABA ethyl ester, N,N-diethoxy PABA ethyl ester, N,N-dimethyl PABA methyl ester, N,N-dimethyl PABA ethyl ester, N,N-dimethyl PABA butyl ester, and N,N-dimethyl PABA 2-ethylhexyl ester; anthranilic acid-based UV absorbers such as homomenthyl-N-acetylanthranilate; salicylic acid-based UV absorbers such as amyl salicylate, menthyl salicylate, homomenthyl salicylate, octyl salicylate, phenyl salicylate, benzyl salicylate, and p-isopropanol phenyl salicylate; cinnamic acid-based UV absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, and glyceryl mono-2-ethylhexanoyl-di-para-methoxycinnamate; silicone-based cinnamic acid-based UV absorbers such as [3-bis(trimethylsiloxy)methylsilyl-1-methylpropyl]-3,4,5-trimethoxycinnamate, [3-bis(trimethylsiloxy)methylsilyl-3-methylpropyl]-3,4,5-trimethoxycinnamate, [3-bis(trimethylsiloxy)methylsilylpropyl]-3,4,5-trimethoxycinnamate, [3-bis(trimethylsiloxy)methylsilylbutyl]-3,4,5-trimethoxycinnamate, [3-tris(trimethylsiloxy)silylbutyl]-3,4,5-trimethoxycinnamate, and [3-tris(trimethylsiloxy)silyl-1-methylpropyl]-3,4-dimethoxycinnamate; benzophenone-based UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; UV absorbers such as 3-(4'-methylbenzylidene)-d,l-camphor, 3-benzylidene-d,l-camphor, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, and 5-(3,3-dimethyl-2-norbornylidene)-3-pentan-2-one; organic acids such as acyl sarcosine acid (e.g., sodium lauroyl sarcosinate), glutathione, citric acid, malic acid, tartaric acid, and lactic acid; vitamins such as vitamin A and derivatives thereof, vitamin B such as vitamin B6 hydrochloride, vitamin B6 tripalmitate, vitamin B6 dioctanoate, vitamin B2 and derivatives thereof, vitamin B12, and vitamin B15 and derivatives thereof, vitamin E such as α-tocopherol, β-tocopherol, γ-tocopherol, and vitamin E acetate, vitamin D, vitamin H, pantothenic acid, pantethine, nicotinamide, and benzyl nicotinate; various agents such as γ-oryzanol, allantoin, glycyrrhizic acid (salt), glycyrrhizic acid and derivatives thereof, tranexamic acid and derivatives thereof [examples of tranexamic acid derivatives include: dimers of tranexamic acid (e.g., hydrochloride trans-4-(trans-aminomethylcyclohexanecarbonyl)aminomethylcyclohexane carboxylic acid), esters of tranexamic acid and hydroquinone (e.g., trans-4-aminomethylcyclohexane carboxylate-4'-hydroxyphenyl ester), esters of tranexamic acid and gentisic acid (e.g., 2-(trans-4-aminomethylcyclohexylcarbonyloxy)-5-hydroxybenzoic acid and salts thereof), amides of tranexamic acid (e.g., trans-4-aminomethylcyclohexanecarboxylic acid methylamide and salts thereof, trans-4-(P-methoxyvinzoyl)-aminomethylcyclohexanecarboxylic acid and salts thereof, trans-4-guanidinomethylcyclohexane carboxylic acid and salts thereof), hinokitiol, bisabolol, eucalypton, thymol, inositol, saponins such as saiko saponin, *ginseng* saponin, *Luffa cylindrica* saponin, and *Sapindus mukorossi* saponin, pantothenyl ethyl ether, ethinylestradiol, tranexamic acid, arbutin, cepharanthine, and placenta extract; plant extracts such as *Rumex japonicus, Sophora flavescens, Nuphar japonica*, orange, sage, *Achillea alpina, Malva varmauritiana, Swertia japonica*, thyme, *Angelica acutiloba*, spruce, birch, *Equisetum arvense, Luffa cylindrica*, marronnier, *Saxifraga stolonifera, arnica*, lily, artemisia, Chinese peony, aloe, *Gardenia jasminoides*, and *Chamaecyparis pisifera*; pigments; porous and/or water-absorbent powders (e.g., starches obtained from corns or potatoes, powders of anhydrous silicic acid, talc, kaolin, magnesium aluminum silicate, and calcium alginate); non-ionic activators such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyoxyethylene alkyl ether, polyglycol diether, lauroyl diethanolamide, fatty acid isopropanolamide, maltitol hydroxy fatty acid ether, alkylated polysaccharides, alkylglucoside, and sugar ester; cationic surfactants such as stearyltrimethylammonium chloride, benzalkonium chloride, and laurylamine oxide, anionic surfactants such as sodium palmitate, sodium laurate, sodium laurate, potassium lauryl sulfate, alkyl sulfate triethanolamine ether, Turkey red oil, linear dodecylbenzene sulfonate, polyoxyethylene hardened castor oil maleic acid, and acyl methyl taurate; amphoteric surfactants; neutralizers; preservatives; fragrances; and pigments.

The method for producing the W/O/W emulsion composition of the present invention is not particularly limited, and the W/O/W emulsion composition can be produced by common methods. For example, a W/O emulsion produced by stirring and mixing with an emulsification equipment such as a disper mixer is prepared, and then the W/O emulsion and an outer aqueous phase comprising an alkyl-modified carboxyvinylpolymer is mixed and emulsified to obtain a W/O/W emulsion composition.

EXAMPLES

The present invention is described in more details based on the examples in the following; however, the present invention is not limited thereto. The blending amounts are in "% by weight".

Before describing the examples, test methods and evaluation methods adopted for the examples and comparative examples are described.

[Viscosity Measurement]
When the viscosity was 50000 mPa·s or greater, the viscosity was measured with Viscometer TVB-15(TVH), manufactured by TOKI SANGYO CO., LTD., Rotor No. 7, at 10 rpm.

Moreover, when the viscosity was less than 50000 mPa·s, the viscosity was measured with Viscometer TVB-15 (TVM), manufactured by TOKI SANGYO CO., LTD., Rotor No. 4, at 12 rpm.

[Phase-State Confirmation]
The phase state was confirmed with an optical microscope.

[Stability Evaluation]
The samples obtained in the examples and comparative examples were filled in 50 ml sample tubes (glass bottle) respectively. After leaving them to stand still at −10° C., room temperature and 50° C. for two weeks, they were observed with eyes and a microscope for evaluation.
(Evaluation Criteria)
A: The sample is not separated at all, and emulsion particles are stable.
B: The sample is not separated, but emulsion particles are partially collapsed.
C: The sample is not separated, but emulsion particles are collapsed.
D: The sample is separated, and emulsion particles are collapsed too.

First, the present inventors examined the effect of the surfactant species and the oil species in the oil phase on W/O/W formation.

The results are shown in Table 1.

TABLE 1

|  |  |  | Test example | | |
|---|---|---|---|---|---|
|  |  |  | 1-1 | 1-2 | 1-3 |
| Inner aqueous phase |  | Ion-exchanged water | 5 | 5 | 5 |
|  | Osmotic pressure regulator | Sodium L-glutamate | 0.1 | 0.1 | 0.1 |
| Oil phase | Oil component | Methylpolysiloxane | 3.0 | 3.0 | 11.0 |
|  |  | Methylphenyl polysiloxane | — | — | 5.0 |
|  |  | Olefin oligomer | 3.0 | 3.0 | — |
|  |  | Isododecane | 5.0 | 5.0 | — |
|  |  | Isohexadecane | 5.0 | 5.0 | — |
|  | Surfactant | PEG-9 polydimethyl siloxyethyl dimethicone | 0.6 | — | 0.6 |
|  |  | Polyethylene glycol distearate | — | 0.6 | — |
| Outer aqueous phase |  | Ion-exchanged water | Balance | Balance | Balance |
|  |  | Alkyl-modified carboxyvinyl polymer | 0.10 | 0.10 | 0.10 |
|  |  | Potassium hydroxide | 0.1 | 0.1 | 0.1 |
|  | Polyol | Glycerin | 3 | 3 | 3 |
|  |  | 1,3-butylene glycol | 2 | 2 | 2 |
|  |  | Dipropylene glycol | 5 | 5 | 5 |
|  | Others | Carbomer | 0.15 | 0.15 | 0.15 |
|  |  | Phase state | O/W | W/O parts could not be formed | W/O/W |
|  |  | Viscosity after 1 day from production (mPa · s) | 34750 | — | 66600 |

[Sensory Test Evaluation of Feel Upon Use]
30 male and 30 female panelists (60 panelists in total) used the samples obtained in the examples and comparative examples to evaluate freshness based on the following criteria.
[Feel Upon Use]
A: 30 or more panelists felt freshness of skin.
B: 10 to 29 panelists felt freshness of skin.
C: 5 to 9 panelists felt freshness of skin.
D: 4 or less panelists felt freshness of skin.

As is obvious from the results shown in Table 1, when the hydrocarbon oil is adopted as the main oil component in the oil phase (Test examples 1-1, 1-2), it may become difficult to form the W/O/W phase depending on the oil type. Whereas, when the silicone-based surfactant (PEG-9 polydimethylsiloxyethyl dimethicone) is used together with the silicone oil as the oil component, the W/O/W phase is formed and thickness becomes remarkable.

As described, it is not sufficient to simply adopt the emulsifiable oil type and surfactant in order to form the W/O/W phase. It is necessary to use a specific silicone-based surfactant in order to form the W/O/W phase with the silicone oil in particular.

Next, the present inventors studied on the osmotic pressure regulator. The results are shown in Table 2.

TABLE 2

| | | | Test example | | | | |
|---|---|---|---|---|---|---|---|
| | | | 1-3 | 2-1 | 2-2 | 2-3 | 2-4 |
| Inner aqueous phase | | Ion-exchanged water | 5 | 5 | 5 | 5 | 5 |
| | Osmotic pressure regulator | Sodium L-glutamate | 0.1 | — | — | — | — |
| | | Sodium chloride | — | 0.1 | — | — | — |
| | | Maltitol | — | — | 1.4 | — | — |
| | | Sorbitol | — | — | — | 1.4 | — |
| | | PEG20000 | — | — | — | — | 1.0 |
| Oil phase | Oil component | Methylpolysiloxane | 11 | 11 | 11 | 11 | 11 |
| | | Methylphenyl polysiloxane | 5 | 5 | 5 | 5 | 5 |
| | Surfactant | PEG-9 polydimethyl siloxyethyl dimethicone | 0.6 | 0.6 | 0.6 | 0.6 | 0.6 |
| Outer aqueous phase | | Ion-exchanged water | Balance | Balance | Balance | Balance | Balance |
| | | Alkyl-modified carboxyvinyl polymer | 0.10 | 0.10 | 0.10 | 0.10 | 0.10 |
| | | Potassium hydroxide | 0.1 | 0.1 | 0.1 | 0.1 | 0.1 |
| | Polyol | Glycerin | 3 | 3 | 3 | 3 | 3 |
| | | 1,3-butylene glycol | 2 | 2 | 2 | 2 | 2 |
| | | Dipropylene glycol | 5 | 5 | 5 | 5 | 5 |
| | Others | Carbomer | 0.15 | 0.15 | 0.15 | 0.15 | 0.15 |
| Evaluation | | Feel upon use | A | A | A | A | A |
| | | Phase state | W/O/W | W/O/W | W/O/W | W/O/W | W/O/W |
| | | Viscosity after 1 day from production | 66600 | 110000 | 125000 | 119000 | 19000 |
| | | Stability (room temperature) | A | A | A | A | A |

Table 2 shows that not only the electrolytes such as sodium L-glutamate and sodium chloride, but also polyols represented by sugar alcohols such as maltitol and sorbitol act well as the osmotic pressure regulator. However, since osmotic pressure depends on ion concentration, those that have a relatively large molecular weight and are non-electrolytes such as maltitol and sorbitol need to be blended in a relatively large amount.

Furthermore, the present inventors used γ-cyclodextrin as the osmotic pressure regulator, and varied the blending amount thereof. The results are shown in Table 3.

TABLE 3

| | | | Test example | | |
|---|---|---|---|---|---|
| | | | 3-1 | 3-2 | 3-3 |
| Inner aqueous phase | | Ion-exchanged water | 5 | 5 | 5 |
| | Osmotic pressure regulator | γ-cyclodextrin | 0.1 | 0.3 | 0.5 |
| Oil phase | Oil component | Methylpolysiloxane | 11 | 11 | 11 |
| | | Methylphenyl polysiloxane | 5 | 5 | 5 |
| | Surfactant | PEG-9 polydimethyl siloxyethyl dimethicone | 0.6 | 0.6 | 0.6 |
| Outer aqueous phase | | Ion-exchanged water | Balance | Balance | Balance |
| | | Alkyl-modified carboxyvinyl polymer | 0.10 | 0.10 | 0.10 |
| | | Potassium hydroxide | 0.1 | 0.1 | 0.1 |
| | Polyol | Glycerin | 3 | 3 | 3 |
| | | 1,3-butylene glycol | 2 | 2 | 2 |
| | | Dipropylene glycol | 5 | 5 | 5 |
| | Others | Carbomer | 0.15 | 0.15 | 0.15 |
| Evaluation | | Feel upon use | A | A | A |
| | | Phase state | W/O/W | W/O/W | W/O/W |
| | 1 day after production | pH | 6.15 | 6.1 | 6.05 |
| | | Viscosity | 17600 | 20710 | 25060 |
| | 4 weeks at room temperature | pH | 6.082 | 6.012 | 6.001 |
| | | Viscosity | 14550 | 18900 | 22960 |
| | 4 weeks at −10° C. | pH | 6.124 | 6.038 | 6.017 |
| | | Viscosity | 15170 | 20300 | 23960 |
| | 4 weeks at 50° C. | pH | 6.045 | 5.979 | 5.94 |
| | | Viscosity | 14570 | 20530 | 26410 |

As is obvious from Table 3, when the concentration of the osmotic pressure regulator in the inner phase increases, the osmotic pressure difference between the outer aqueous phase becomes larger; therefore, the viscosity tends to increase.

Moreover, the present inventors studied on stability of the composition of the present invention at low temperature. The results are shown in Table 4.

TABLE 4

|  |  |  | Test example | | | |
|---|---|---|---|---|---|---|
|  |  |  | 4-1 | 4-2 | 4-3 | 4-4 |
| Inner aqueous phase | Ion-exchanged water | | 5 | 5 | 5 | 5 |
| | Osmotic pressure regulator | Sodium L-glutamate | 0.10 | 0.1 | 0.15 | 0.15 |
| | Others | 4-MSK | 1.0 | 1.0 | 1.0 | 1.0 |
| Oil phase | Oil component | Methylpolysiloxane | 5.4 | 5.4 | 5.4 | 5.4 |
| | | Methylphenyl polysiloxane | 2.0 | 2.0 | 2.0 | 2.0 |
| | | Cetyl 2-ethylhexanoate | 2.0 | 2.0 | 2.0 | 2.0 |
| | | Isohexadecane | 3.0 | 3.0 | 3.0 | 3.0 |
| | Surfactant | PEG-9 polydimethyl siloxyethyl dimethicone | 0.6 | 0.6 | 0.8 | 0.8 |
| Outer aqueous phase | Ion-exchanged water | | Balance | Balance | Balance | Balance |
| | Alkyl-modified carboxyvinyl polymer | | 0.10 | 0.10 | 0.10 | 0.10 |
| | Potassium hydroxide | | 0.1 | 0.1 | 0.1 | 0.1 |
| | Polyol | Glycerin | 3 | 11.0 | 3 | 11.0 |
| | | 1,3-butylene glycol | 2 | 1.0 | 2 | 1.0 |
| | | Dipropylene glycol | 5 | 9.0 | 5 | 9.0 |
| | Others | Carbomer | 0.15 | 0.15 | 0.15 | 0.15 |
| Evaluation | Feel upon use | | A | A | A | A |
| | Phase state | | W/O/W | W/O/W | W/O/W | W/O/W |
| | 1 day after production | pH | 5.61 | 5.61 | 5.6 | 5.63 |
| | | Viscosity | 5470 | 5950 | 40400 | 46000 |
| | 4 weeks at room temperature | pH | 5.68 | 5.73 | 5.64 | 5.71 |
| | | Viscosity | 11340 | 16390 | 43500 | 50800 |
| | 4 weeks at −10° C. | pH | — | 5.74 | 5.74 | 5.76 |
| | | Viscosity | Separated | 16460 | 45400 | 56800 |
| | 4 weeks at 50° C. | pH | 5.72 | 5.76 | 5.67 | 5.71 |
| | | Viscosity | 10880 | 10240 | 34100 | 32700 |

In the present Test examples, 1% by mass of 4MSK (potassium 4-methoxysalicylate) is added as the agent. As is obvious from Test examples 4-1 and 4-2, freezing resistance improves by increasing the amount of polyol in the outer aqueous phase. When the amount of polyol is increased, however, the osmotic pressure difference between the inner aqueous phase becomes smaller; therefore, increase in viscosity is suppressed.

Whereas, referring to Test examples 4-3 and 4-4, both of freezing resistance and viscosity can be increased by increasing the amount of the surfactant in the oil phase.

Next, the present inventors varied the types of the surfactants, and studied thereon. The results are show in Table 5.

TABLE 5

|  |  |  | Test example 5-1 |
|---|---|---|---|
| Inner aqueous phase | Ion-exchanged water | | 0.8 |
| | Osmotic pressure regulator | Sodium L-glutamate | 0.2 |
| Oil phase | Oil component | Methylpolysiloxane | 11.0 |
| | | Methylphenyl polysiloxane | 5.0 |
| | Surfactant | PEG-10 dimethicone | 0.6 |
| Outer aqueous phase | Ion-exchanged water | | Balance |
| | Alkyl-modified carboxyvinyl polymer | | 0.10 |
| | Potassium hydroxide | | 0.1 |
| | Polyol | Glycerin | 3 |
| | | 1,3-butylene glycol | 2 |
| | | Dipropylene glycol | 5 |
| | Others | Carbomer | 0.15 |
| Evaluation | Feel upon use | | A |
| | Phase state | | W/O/W |
| | Immediately after production | Emulsion particle size | ~20 |
| | | Viscosity | 36330 |
| | 4 weeks at room temperature | pH | 5.922 |
| | | Viscosity | 29680 |
| | 4 weeks at −10° C. | pH | 5.912 |
| | | Viscosity | 25070 |
| | 4 weeks at 50° C. | pH | 5.912 |
| | | Viscosity | 30810 |

A formulation example of the present invention is shown in Table 6.

TABLE 6

|  |  |  | Test example 6-1 |
|---|---|---|---|
| Inner aqueous phase | Ion-exchanged water | | 5 |
| | Osmotic pressure regulator | Sodium L-glutamate | 0.15 |
| | Others | 4-MSK | 1.0 |
| Oil phase | Oil component | Methylpolysiloxane | 11 |
| | | Methylphenyl polysiloxane | 5 |
| | | Vitamin E acetate | 0.05 |

TABLE 6-continued

|  |  |  | Test example 6-1 |
|---|---|---|---|
|  | Surfactant | PEG-9 polydimethyl siloxyethyl dimethicone | 0.6 |
| Outer aqueous phase | | Ion-exchanged water | Balance |
| | | Alkyl-modified carboxyvinyl polymer | 0.1 |
| | | Potassium hydroxide | 0.12 |
| | Polyol | Glycerin | 3.0 |
| | | 1,3-butylene glycol | 5 |
| | | Dipropylene glycol | 9.0 |
| | Others | Carbomer | 0.1 |
| Evaluation | | Feel upon use | A |
| | | Phase state | W/O/W |
| | Immediately after production | pH | 6.63 |
| | | Viscosity | 47600 |

What is claimed is:

1. A W/O/W emulsion composition comprising:
an inner aqueous phase,
an oil phase in which the inner aqueous phase is dispersed, and
an outer aqueous phase in which the oil phase is dispersed,
wherein:
the inner aqueous phase comprises an osmotic pressure regulator that prepares the inner aqueous phase to have a higher osmotic pressure than the outer aqueous phase;
the oil phase comprises a silicone oil that is 0.7 times by mass or greater of the total oil phase, and a silicone-based surfactant having a silicone skeleton as a main skeleton and a hydrophilic group in a side chain;
the outer aqueous phase comprises a polyol and an alkyl-modified carboxyvinyl polymer, and
wherein the polyol added to the outer aqueous phase is two or more types selected from glycerin, 1,3-butylene glycol and dipropylene glycol, and the amount of polyol in the outer aqueous phase is 10% by mass to 21% by mass.

2. The W/O/W emulsion composition of claim 1, wherein the osmotic pressure regulator is one type or two or more types selected from sodium chloride, maltitol, sorbitol γ-cyclodextrin and polyethylene glycol.

3. The W/O/W emulsion composition of claim 1, wherein the silicone surfactant is PEG-9 polydimethylsiloxyethyl dimethicone or PEG-10 dimethicone.

4. The W/O/W emulsion composition of claim 1, wherein the polyol added to the outer aqueous phase is three types selected from glycerin, 1,3-butylene glycol and dipropylene glycol.

5. The W/O/W emulsion composition of claim 1, wherein the amount of silicone surfactant in the total composition is 0.1% by mass to 7% by mass.

6. The W/O/W emulsion composition of claim 1, wherein the inner aqueous phase contains potassium salt of 4-methoxysalicylic acid.

* * * * *